US00PP32951P3

(12) United States Plant Patent
Meulenbroek

(10) Patent No.: US PP32,951 P3
(45) Date of Patent: Apr. 6, 2021

(54) STRAWBERRY PLANT NAMED 'FD 1604'

(50) Latin Name: ***Fragaria* x *ananassa***
Varietal Denomination: FD 1604

(71) Applicant: Egbertus Joseph Meulenbroek, Zetten (NL)

(72) Inventor: Egbertus Joseph Meulenbroek, Zetten (NL)

(73) Assignee: FRESH FORWARD HOLDING B.V., Eck en Wiel (NL)

( * ) Notice: Subject to any disclaimer, the term of this patent is extended or adjusted under 35 U.S.C. 154(b) by 0 days.

(21) Appl. No.: 16/501,605

(22) Filed: May 7, 2019

(65) Prior Publication Data

US 2020/0359538 P1 Nov. 12, 2020

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409
See application file for complete search history.

(56) References Cited

PUBLICATIONS

UPOV hit on Strawberry plant named, 'FD 1604', QZ PBR 2016/1226, Aug. 16, 2016.*
UPOV hit on Strawberry plant named 'FD 1604', QZ PBR 2016/1226, published Aug. 16, 2016.*

* cited by examiner

*Primary Examiner* — Anne Marie Grunberg
(74) *Attorney, Agent, or Firm* — C. Anne Whealy

(57) ABSTRACT

A new and distinct cultivar of Strawberry plant named 'FD 1604', characterized by its compact, upright to semi-upright plant habit; moderately vigorous to vigorous growth habit; uniform fruit ripening; medium-sized conical to long conical fruits that are glossy and red in color; pleasant fruit aroma and sweet taste; and excellent fruit postharvest longevity.

3 Drawing Sheets

Botanical designation: *Fragaria* x *ananassa*.
Cultivar denomination: 'FD 1604'.

BACKGROUND OF THE INVENTION

The present Invention relates to a new and distinct cultivar of Strawberry plant, botanically known as *Fragaria* x *ananassa* and hereinafter referred to by the name 'FD 1604'.

The new Strawberry plant is a product of a planned breeding program conducted by the Inventor in Eck en Wiel, The Netherlands. The objective of the breeding program was to develop new Strawberry plants with good fruit quality, ease of harvesting, high yield, large fruits and good postharvest longevity.

The new Strawberry plant originated from a cross-pollination by the Inventor during the summer of 2011 in Eck en Wiel, The Netherlands of a proprietary selection of *Fragaria* x *ananassa* identified as code designation D1930-013, not patented, as the female, or seed, parent with a proprietary selection of *Fragaria* x *ananassa* identified as code designation D1930-237, not patented, as the male, or pollen, parent. The new Strawberry plant was discovered and selected by the Inventor as a single plant from within the progeny of the stated cross-pollination in a controlled environment in Eck en Wiel, The Netherlands during the summer of 2012.

Asexual reproduction of the new Strawberry plant by runner cuttings in a controlled environment at Eck en Wiel, The Netherlands since the autumn of 2012 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FD 1604'. These characteristics in combination distinguish 'FD 1604' as a new and distinct Strawberry plant:

1. Compact, upright to semi-upright plant habit.
2. Moderately vigorous to vigorous growth habit
3. Uniform fruit ripening.
4. Medium-sized conical to long conical fruits that are glossy and red in color.
5. Pleasant fruit aroma and sweet taste.
6. Excellent fruit postharvest longevity.

Plants of the new Strawberry differ primarily from plants of the female parent selection in the following characteristics:

1. Plants of the new Strawberry are more upright and not as spreading as plants of the female parent selection.

2. Fruits of plants of the new Strawberry are conical to long conical in shape whereas fruits of plants of the female parent selection are conical in shape.
3. Fruits of plants of the new Strawberry are lighter red in color than fruits of plants of the female parent selection.

Plants of the new Strawberry differ primarily from plants of the male parent selection in the following characteristics:

1. Plants of the new Strawberry are less vigorous than plants of the male parent selection.
2. Leaves of plants of the new Strawberry are darker green in color than leaves of plants of the male parent selection.
3. Fruits of plants of the new Strawberry are red in color whereas fruits of plants of the male parent selection are orange red in color.

Plants of the new Strawberry can be compared to plants of *Fragaria* x *ananassa* 'Seascape', disclosed in U.S. Plant Pat. No. 7,614. In side-by-side comparisons, plants of the new Strawberry differ primarily from plants of 'Seascape' in the following characteristics:

1. Fruits of plants of the new Strawberry are conical to long conical in shape whereas fruits of plants of 'Seascape' are cordate to wedged-shaped.
2. Fruits of plants of the new Strawberry are lighter red in color than fruits of plants of 'Seascape'.
3. Fruits of plants of the new Strawberry are firmer than fruits of plants of 'Seascape'.

Plants of the new Strawberry can also be compared to plants of *Fragaria* x *ananassa* 'Mara Des Bois', disclosed in U.S. Plant Pat. No. 8,517. In side-by-side comparisons, plants of the new Strawberry differ primarily from plants of 'Mara Des Bois' in the following characteristics:

1. Fruits of plants of the new Strawberry are conical to long conical in shape whereas fruits of plants of 'Mara Des Bois' are ovoid to rhomboid in shape.
2. Fruits of plants of the new Strawberry are larger than fruits of plants of 'Mara Des Bois'.
3. Fruit surfaces of plants of the new Strawberry are more even than fruit surfaces of plants of 'Mara Des Bois'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a side perspective view of typical fruiting plants of 'FD 1604' grown in a greenhouse environment.

The photograph on the second sheet is a close-up view of typical developing and developed fruits of 'FD 1604'.

The photograph on the third sheet is a close-up view of typical harvested fruits of 'FD 1604'.

DETAILED BOTANICAL DESCRIPTION

The following observations and measurements describe plants grown in 2.5-liter containers during the spring and summer in a glass-covered greenhouse in Stevensbeek, Noord-Brabant, The Netherlands and under cultural practices typical of commercial Strawberry production. During the production of the plants, day temperatures ranged from 12° C. to 23° C. and night temperatures ranged from 8° C. to 12° C. Plants were one year old when the photographs were taken and ten weeks from planting when the description was taken. In the following description, color references are made to The Royal Horticultural Society Colour Chart, 2001 Edition, except where general terms of ordinary dictionary significance are used.

Botanical classification: *Fragaria* x *ananassa* 'FD 1604'.

Parentage:

*Female, or seed, parent*.—Proprietary selection of *Fragaria* x *ananassa* identified as code designation D1930-013, not patented.

*Male, or pollen, parent*.—Proprietary selection of *Fragaria* x *ananassa* identified as code name D1930-237, not patented.

Propagation:

*Type*.—By runner cuttings.

*Time to initiate roots, summer*.—About one to four days at soil temperatures about 15° C. and ambient temperatures about 17° C.

*Time to produce a rooted young plant, summer*.—About two to three weeks at soil temperatures ranging from 15° to 20° C. and ambient temperatures about 17° C.

*Root description*.—Medium in thickness, fibrous; typically cream white to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; compact, upright to semi-upright plant habit; leaves basal; moderately vigorous to vigorous growth habit; moderately to densely foliated; moderate growth rate.

*Plant height*.—About 25 cm to 30 cm.

*Plant diameter*.—About 30 cm to 35 cm.

*Stolon texture*.—Sparsely pubescent.

*Stolon color*.—Close to 144B.

Leaf description:

*Arrangement and appearance*.—Basal rosette; compound with typically three leaflets per leaf; leaves, non-variegated; foliage, moderately dense to dense.

*Leaflet length*.—About 9 cm to 12 cm.

*Leaflet width*.—About 8 cm to 11 cm.

*Leaflet shape*.—Broadly ovate; concave in cross-section.

*Leaflet apex*.—Obtuse to acute.

*Leaflet base*.—Obtuse to rounded.

*Leaflet margin*.—Serrate to lobed.

*Leaflet texture and luster, upper surface*.—Pubescent; moderately glossy; blistering, absent to weak.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to 137A; venation, close to 144B. Fully expanded leaflets, lower surface: Close to 138A; venation, close to 144B.

*Petioles*.—Length: About 9 cm to 15 cm. Diameter: About 2.5 mm to 5 mm. Texture, upper and lower surfaces: Pubescent; attitude of hairs, horizontal. Color, upper and lower surfaces: Close to 145A.

Flower description:

*Flower form and flowering habit*.—Rotate flowers arranged singly at lateral apices; flowers held at the foliar plane; flowers are self-fertile.

*Fragrance*.—None detected.

*Natural flowering season*.—Plants flower in June to frost in The Netherlands, flowering remontant; numerous flowers develop during the flowering season.

*Flower diameter*.—About 2.5 cm to 3.5 cm.

*Flower depth* (*height*).—About 5 mm to 10 mm.

*Petals*.—Arrangement: Single whorl of six petals; petals imbricate. Length: About 8 mm to 12 mm. Width: About 8 mm to 12 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of eight to twelve sepals; calyx, star-shaped; calyx adherence is weak to moderate; position of calyx attachment, slightly inserted to level; sepals are orientated upwards from the fruit. Calyx length: About 1 cm to 1.5 cm. Calyx diameter: About 2.5 cm to 4 cm. Length: About 5 mm to 8 mm. Width: About 3 mm to 5 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 2 cm to 5 cm. Diameter: About 1 mm to 2 mm. Strength: Strong. Aspect: About 90° from peduncle axis. Texture: Pubescent; attitude of hairs, horizontal. Color: Close to 144B.

*Reproductive organs*.—Stamens: Quantity per flower: About 25. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruits: Quantity: About six to ten per truss; about 60 to 70 fruits develop per plant during the fruiting season; plants produce fruit from the end of June until frost. Post-harvest longevity: About seven to ten days at 7° C. Length: About 2 cm to 5 cm. Diameter: About 2 cm to 3.5 cm. Shape: Fruits are relatively medium-sized and are conical to long conical in shape; primary fruits may be somewhat broader and less conical than secondary fruits. Core cavity size: Less than 2 mm. Fruit weight per fruit, first quality: About 17.3 g. Fruit weight per plant, first quality: About 974 g. Firmness: Medium firm. Fragrance, taste: Pleasant; good balance between sweetness and acidity; aromatic. Degrees brix: About 10.3. Luster: Uniformly glossy. Surface unevenness: Smooth. Color, surface: Close to 42B; even. Color, flesh: Close to 30B to 30A. Achene density: Medium. Achene quantity per fruit: About 150 to 300. Achene position: Level with fruit surface. Achene weight: About 0.591 grams/1,000 seeds. Achene color: Close to 42B.

Pathogen and pest resistance: To date, plants of the new Strawberry have not been observed to be resistant to pathogens and pests common to Strawberry plants.

It is claimed:

1. A new and distinct Strawberry plant named 'FD 1604' as illustrated and described.

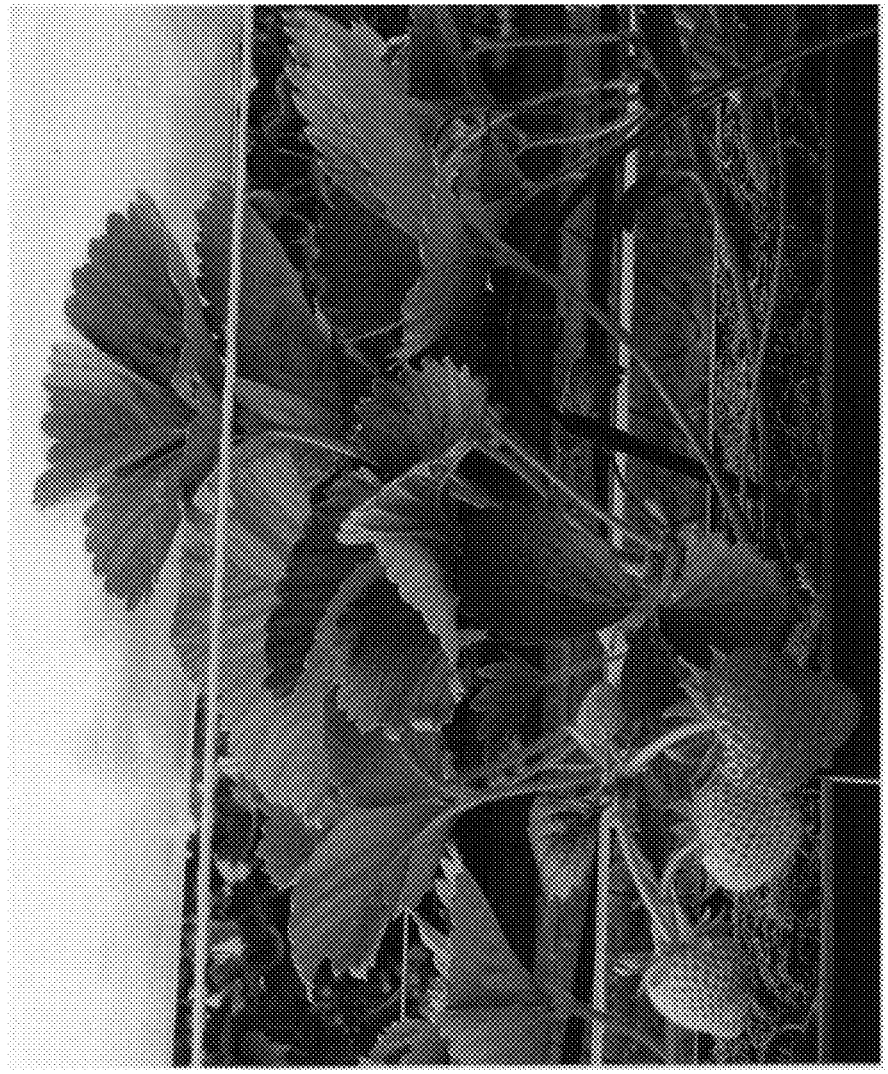

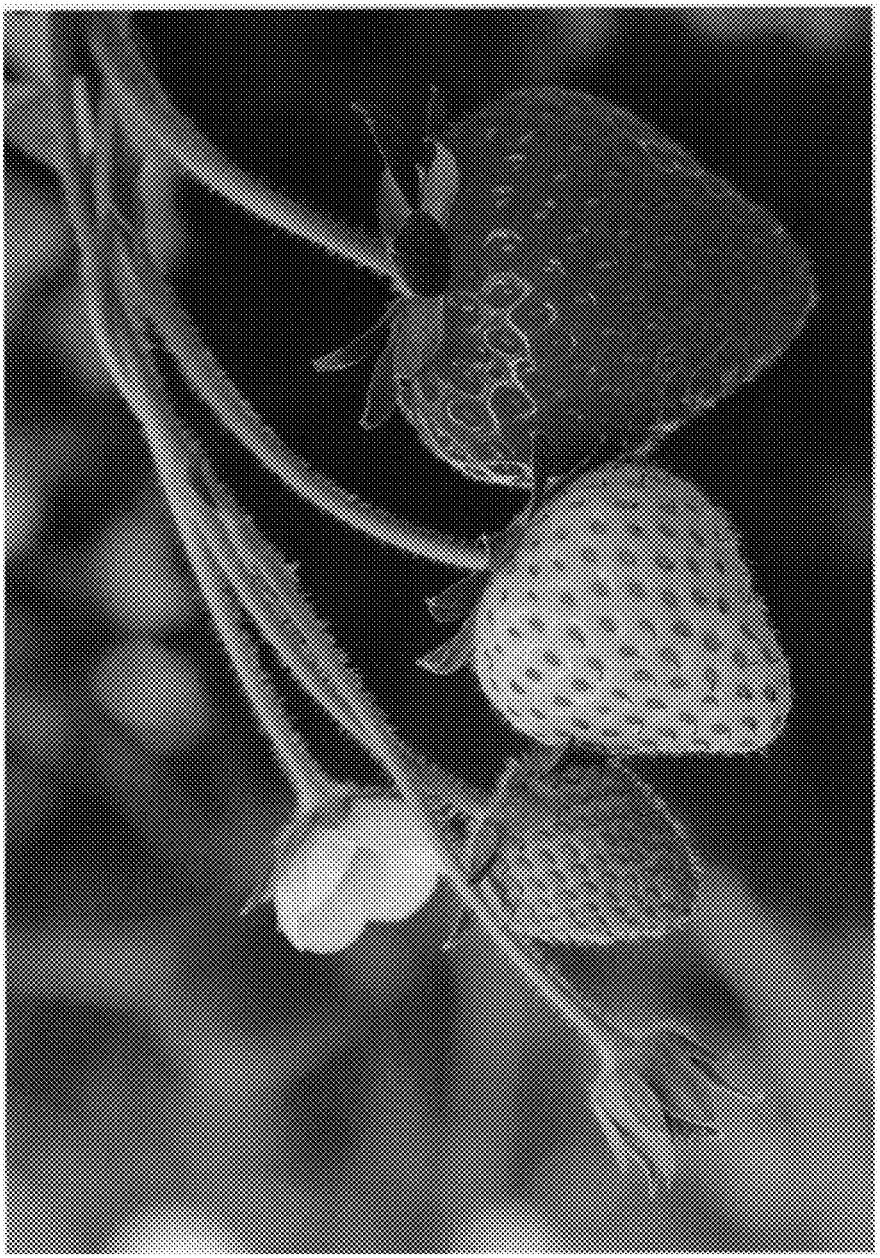

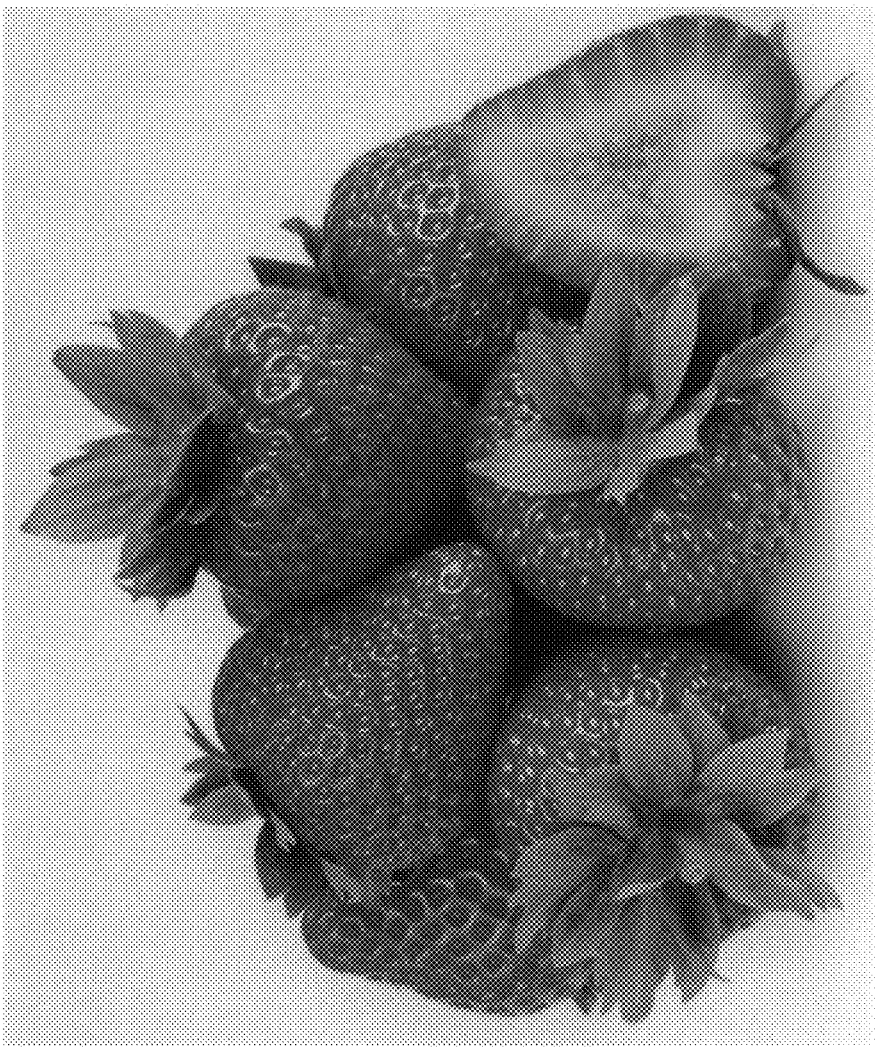

* * * * *